US011363945B2

(12) United States Patent
Hosoda et al.

(10) Patent No.: US 11,363,945 B2
(45) Date of Patent: Jun. 21, 2022

(54) OMNI-DIRECTIONAL VIEWING APPARATUS

(71) Applicant: The General Hospital Corporation, Boston, MA (US)

(72) Inventors: Masaki Hosoda, Cambridge, MA (US); Seemantini K. Nadkarni, Cambridge, MA (US); Milen Shishkov, Watertown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/309,627

(22) Filed: Jun. 19, 2014

(65) Prior Publication Data

US 2014/0378846 A1 Dec. 25, 2014

Related U.S. Application Data

(60) Provisional application No. 61/836,716, filed on Jun. 19, 2013, provisional application No. 61/905,893, (Continued)

(51) Int. Cl.
*A61B 5/00* (2006.01)
*A61B 1/00* (2006.01)
(Continued)

(52) U.S. Cl.
CPC ........ *A61B 1/3137* (2013.01); *A61B 1/00096* (2013.01); *A61B 1/00165* (2013.01); (Continued)

(58) Field of Classification Search
CPC .............. A61B 1/3171; A61B 1/00096; A61B 1/00165; A61B 5/0066; A61B 5/0084; (Continued)

(56) References Cited

U.S. PATENT DOCUMENTS 5,214,538 A 5/1993 Lobb
5,353,798 A 10/1994 Sieben
(Continued)

FOREIGN PATENT DOCUMENTS

JP H1156786 A 3/1999
JP 2010266326 A 11/2010
(Continued)

OTHER PUBLICATIONS

John A. Gilbert; "Recent Developments in Radial Metrology: A Computer-Based Optical Method for Profiling Cavities;" http://www.eng.uah.edu/~jag/resume/Presentations/PRES48.pdf; pp. 1-6.
(Continued)

*Primary Examiner* — Patricia J Park
(74) *Attorney, Agent, or Firm* — Quarles & Brady LLP (57) ABSTRACT

There is provided a new apparatus, system, and method of use for laser speckle imaging that allows for omni-directional viewing. The omni-directional viewing can include a reflector and switches configured for switching the illumination on the luminal tissue such that the light reflected from the luminal tissue at any given time is reflected from one or more substantially non-overlapping sections of a luminal tissue. This apparatus may be particularly useful for tissue analysis such as analysis of vulnerable plaque.

22 Claims, 6 Drawing Sheets

Related U.S. Application Data filed on Nov. 19, 2013, provisional application No. 61/934,518, filed on Jan. 31, 2014, provisional application No. 61/934,454, filed on Jan. 31, 2014.

(51) Int. Cl.
*A61B 1/313* (2006.01)
*A61B 5/02* (2006.01)

(52) U.S. Cl.
CPC .......... *A61B 5/0066* (2013.01); *A61B 5/0084* (2013.01); *A61B 5/02007* (2013.01); *A61B 5/6852* (2013.01); *A61B 5/6876* (2013.01)

(58) Field of Classification Search
CPC .. A61B 5/02007; A61B 5/6852; A61B 5/6876
See application file for complete search history.

(56) References Cited

U.S. PATENT DOCUMENTS

| | | | |
|---|---|---|---|
| 6,527,708 B1 | 3/2003 | Nakamura et al. | |
| 6,788,861 B1 | 9/2004 | Utsui et al. | |
| 6,887,196 B2 | 5/2005 | Arai et al. | |
| 6,944,494 B2 | 9/2005 | Forrester et al. | |
| 7,110,124 B2 | 9/2006 | Jensen et al. | |
| 7,113,817 B1 | 9/2006 | Winchester, Jr. et al. | |
| 7,231,243 B2 | 6/2007 | Tearney et al. | |
| 7,783,337 B2 | 8/2010 | Feldman et al. | |
| 7,801,584 B2 | 9/2010 | Iddan et al. | |
| 7,922,655 B2 | 4/2011 | Yasushi et al. | |
| 8,032,200 B2 | 10/2011 | Tearney et al. | |
| 8,226,551 B2 | 7/2012 | Sugimoto | |
| 8,337,400 B2 | 12/2012 | Mizuyoshi | |
| 8,451,452 B2 | 5/2013 | Podoleanu et al. | |
| 8,500,730 B2 | 8/2013 | Lee et al. | |
| 8,509,879 B2 | 8/2013 | Durkin et al. | |
| 8,628,520 B2 | 1/2014 | Sharareh et al. | |
| 2003/0011768 A1* | 1/2003 | Jung | G01J 1/04 356/326 |
| 2004/0114860 A1* | 6/2004 | Dultz | G02B 6/4206 385/31 |
| 2004/0220478 A1 | 11/2004 | Wallace et al. | |
| 2004/0249247 A1 | 12/2004 | Iddan | |
| 2005/0049462 A1 | 3/2005 | Kanazawa | |
| 2006/0118742 A1* | 6/2006 | Levenson | A61B 5/0059 250/559.3 |
| 2007/0078500 A1* | 4/2007 | Ryan | A61B 5/0066 607/88 |
| 2007/0270717 A1* | 11/2007 | Tang | A61B 1/00096 600/585 |
| 2008/0002211 A1 | 1/2008 | Park et al. | |
| 2008/0058629 A1 | 3/2008 | Seibel et al. | |
| 2008/0177145 A1 | 7/2008 | Furnish | |
| 2008/0221388 A1* | 9/2008 | Seibel | A61B 1/0008 600/109 |
| 2008/0262359 A1* | 10/2008 | Tearney | A61B 1/00096 600/476 |
| 2009/0099460 A1* | 4/2009 | Zuluaga | A61B 1/00186 600/478 |
| 2009/0135280 A1* | 5/2009 | Johnston | A61B 1/0005 348/262 |
| 2009/0209834 A1* | 8/2009 | Fine | A61B 5/14551 600/316 |
| 2009/0323076 A1* | 12/2009 | Li | A61B 5/0066 356/479 |
| 2010/0004531 A1* | 1/2010 | Passmore | A61B 5/0066 600/425 |
| 2010/0081873 A1 | 4/2010 | Tanimura et al. | |
| 2010/0134607 A1 | 6/2010 | Ishihara | |
| 2010/0198081 A1 | 8/2010 | Hanlin et al. | |
| 2010/0224796 A1 | 9/2010 | Mertz et al. | |
| 2010/0290059 A1 | 11/2010 | Inoue | |
| 2011/0295061 A1 | 12/2011 | Haramaty et al. | |
| 2011/0319714 A1* | 12/2011 | Roelle | A61B 1/00006 600/118 |
| 2012/0019809 A1* | 1/2012 | Shirley | G01B 11/24 356/51 |
| 2012/0022381 A1 | 1/2012 | Tearney et al. | |
| 2012/0112037 A1* | 5/2012 | Hiramoto | G03B 35/08 250/206 |
| 2012/0130253 A1 | 5/2012 | Nadkarni et al. | |
| 2013/0296695 A1 | 11/2013 | Spencer et al. | |

FOREIGN PATENT DOCUMENTS

| | | |
|---|---|---|
| JP | 2012052882 A | 3/2012 |
| JP | 2013006071 A | 1/2013 |
| WO | 2009070161 A1 | 6/2009 |

OTHER PUBLICATIONS

"Omni-directional viewing catheter for intravascular laser speckle imaging (ILSI);" http://spie.org/PWB/conferencedetails/cardiology#session-20; BIOS, SPIE Photonics West; pp. 1-6.

Von Guillermo H. Kaufmann; "Advances in Speckle Metrology and Related Techniques"; WILEY-VCH 2011; http://www.beck-shop.de/fachbuch/leseprobe/9783527409570_Excerpt_001.pdf; pp. 1-37.

Yasuhiro Honda; "Frontiers in Intravascular Imaging Technologies;" https://circ.ahajournals.org/content/117/15/2024.full; pp. 1-17.

Ou-Yang, M. et al.; "Design and analysis of radial imaging capsule endoscope (RICE) system," Optics Express, vol. 19, No. 5, pp. 4369-4383 Feb. 28, 2011.

Chang, S. et al; "Stationary-fiber rotary probe with unobstructed 360o view for optical coherence tomography," Opt. Let. 36 22 pp. 4392-4394 Nov. 15, 2011.

Mu, X. et al; "MEMS micromirror integrated endoscopic probe for optical coherence tomography bioimaging," Sensors and Actuators A 168 (2011) 202-212.

PCT International Search Report and Written Opinion, PCT/US2014/043276, dated Jan. 6, 2015.

European Patent Office, Supplementary European Search Report, Application No. 14813002.4, dated Mar. 14, 2017.

European Patent Office, Extended Search Report, Application No. 20184795.1, dated Sep. 4, 2020, 7 pages.

Japan Patent Office, Notice of Reasons for Rejection, Application No. 2020-159403, dated Aug. 17, 2021, 6 pages.

* cited by examiner

FOV

At fiber bundle face

OMNI-DIRECTIONAL VIEWING APPARATUS

CROSS-REFERENCE TO RELATED APPLICATIONS

This application claims priority from U.S. Provisional Application Ser. No. 61/836,716 filed Jun. 19, 2013; U.S. Provisional Application Ser. No. 61/905,893 filed Nov. 19, 2013; U.S. Provisional Application Ser. No. 61/934,454 filed Jan. 31, 2014, and U.S. Provisional Application Ser. No. 61/934,518 filed Jan. 31, 2014, the disclosures of each of which are hereby incorporated by reference herein in their entirety.

FIELD OF THE INVENTION

This application relates generally to medical devices and in particular to a device for laser speckle imaging.

BACKGROUND

Acute myocardial infarction is frequently caused by the rupture of coronary plaques with severely compromised viscoelastic properties. A new optical technology termed intravascular laser speckle imaging (ILSI) that evaluates plaque viscoelastic properties, by measuring the Brownian motion of light scattering particles from temporally evolving laser speckle fluctuations, has been developed.

ILSI uses the interference phenomenon known as "speckle" that occurs when coherent light (e.g., laser light) is reflected from a rough or multiply scattering sample onto a detection plane. Due to scattering of photons from and within the sample, different photons travel different distances to the detection plane. As a result, the light reflected or backscattered from the sample, if spatially and temporally coherent, interferes at the detection plane, producing a grainy pattern known as "speckle." Using ILSI, plaque viscoelastic properties can be measures. ILSI has been used, for example, to analyze atherosclerotic plaque in a human aorta to assess the plaque's viscosity. See Tearney's U.S. Pat. No. 7,231,243, herein incorporated by reference in its entirety. ILSI is also described for providing intracoronary LSI for a detection of vulnerable plaque. See Tearney's U.S. Patent Pub. No. 2008/0262359, herein incorporated by reference in its entirety.

However, there is still need for an improved catheter, such as a catheter that provides an ILSI image of the circumference of the human aorta or other lumen. While ISLI images of the circumference of a lumen wall can be viewed by using mechanical, the mechanical rotation of a fiber bundle is complicated and difficult to achieve, because a fiber bundle has many fiber cores and is not suitable to typical optical fiber rotary junction. Additionally, the need for non-overlapping images in ILSI makes it difficult to take circumferential images without using the apparatus as described herein. Thus, rotating the fiber bundle as is provided in visual endoscopes is not generally a viable option for ILSI. Additionally, the high fiber density of fibers over the length of the catheter can contribute to the leakage of light (crosstalk) and thus degrade the signal. Thus, there is also needed an apparatus to provide ILSI signal with reduced crosstalk.

Additionally, unlike conventional angioscopy, laser speckle patterns, formed by interference of coherent light, are highly sensitive to motion Thus, an improved ILSI catheter and method of use is needed.

SUMMARY

According to at least one embodiment of the invention, there is provided an apparatus for tissue analysis, comprising: at least a first and a second waveguide, each configured to illuminate a luminal tissue with coherent or partially coherent light, one or more switches configured for switching the illumination of the first and second waveguides, at least a third waveguide configured to receive light reflected from the luminal tissue and form a series of speckle patterns, and a reflector configured to reflect light from the first and second waveguide on the luminal tissue and to reflect light from the luminal tissue onto the third waveguide, wherein the one or more switches are configured such that the light reflected from the luminal tissue onto the third waveguide at any given time is reflected from one or more substantially non-overlapping sections of a luminal tissue. In some embodiments, the apparatus comprises a catheter.

Other embodiments provide an apparatus for tissue analysis comprising: a multiple faceted pyramidal mirror having at least a first mirror facet and a second mirror facet, a switchable illumination fiber in optical communication with the first mirror facet, and a second switchable illumination fiber in optical communication with the second mirror facet, an optical fiber bundle in optical communication with the multiple faceted pyramidal mirror. When in use, the first and second switchable illumination fibers illuminate a substantially non-overlapping tissue section.

Thus, some embodiments provide a multiple faceted pyramidal mirror is a four-faceted pyramidal mirror having a first mirror facet in optical communication with the first waveguide and a second mirror facet in optical communication with the second waveguide, a third mirror facet in optical communication with a fourth waveguide and a fourth mirror facet in optical communication with a fifth waveguide, wherein the fourth and fifth waveguides are both configured to illuminate a luminal tissue with coherent or partially coherent light. Some other embodiments provide a multiple faceted pyramidal mirror is a six-faceted pyramidal mirror having six mirror facets, each of which are in optical communication with a different waveguide, wherein each of the waveguides are configured to illuminate a luminal tissue with coherent or partially coherent light. Some other embodiments provide a multiple faceted pyramidal mirror is a six-faceted pyramidal mirror having six mirror facets, each of which are in optical communication with a different waveguide, wherein each of the waveguides are configured to illuminate a luminal tissue with coherent or partially coherent light.

In some embodiments, the illumination system is a micro-electro-mechanical systems (MEMS) device where the MEMS switches has one input channel and 2-8 output channels that are computer controlled. In some embodiments, the MEMS system has one input channel and two, three, four, or five output channels.

Embodiments as described herein provide a method of tissue analysis comprising: illuminating at least one first cylindrical section of a lumen wall with coherent or partially coherent light by passing the light through at least one facet of a multiple-faceted pyramidal mirror, receiving light reflected from the first cylindrical section of a lumen wall at the mirror; illuminating at least a second cylindrical section of a lumen wall with coherent or partially coherent light at a time different from the first illuminating step by passing the light through at least a second facet of the multiple-faceted pyramidal mirror, receiving light reflected from the second cylindrical section of a lumen wall at the mirror; receiving light reflected from the mirror at a detector and forming series of speckle patterns; analyzing changes in the speckle patterns at time intervals sufficient to measure changes caused by microscopic motion of objects within the tissue. During this illumination, it is preferably that two adjacent facets of the multiple-faceted pyramidal mirror are not illuminated at the same time. In some embodiments, the optical fiber bundle is adapted to receive light from two substantially non-overlapping sections of a tissue, the light having been reflected from the first and the second switchable illumination fibers. In some embodiments, the apparatus includes a switching system that is adapted to illuminate two or more non-adjacent mirror facets at the same time.

Yet other embodiments provide a method of illuminating a tissue wall comprising: illuminating a first portion of a lumen wall with a first switchable illumination fiber, where the illumination travels through a first facet of a multiple faceted pyramidal mirror, illuminating a second portion of the lumen wall with a second switchable illumination fiber, where the illumination travels through a second facet of the multiple faceted pyramidal mirror. In this method, the circumference of the tissue wall is sequentially illuminated. In some embodiments, the first switchable illumination fiber travels through both a first facet and a third facet of a multiple faceted pyramidal mirror, wherein the first and third facets are not adjacent to each other, and wherein the second switchable illumination fiber travels through both a second and a fourth facet of a multiple faceted pyramidal mirror, wherein the second and fourth facets are not adjacent to each other.

In some embodiments, there is provided a laser speckle imaging catheter comprising: a light source, the apparatus as described herein, and a detector.

Further features of the present invention will become apparent from the following description of exemplary embodiments with reference to the attached drawings.

BRIEF DESCRIPTION OF DRAWINGS

Further objects, features and advantages of the present invention will become apparent from the following detailed description when taken in conjunction with the accompanying figures showing illustrative embodiments of the present invention.

FIGS. 1A-1B.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

DETAILED DESCRIPTION OF THE INVENTION

ILSI can be conducted in living animals via an intravascular catheter that permitted single area evaluation of the coronary wall. In an exemplary ILSI system, the emitted beam from a laser source is coupled with a single mode fiber used as an illumination fiber in free space. This illumination fiber and a fiber bundle (FB) are incorporated in an ILSI catheter. The fiber bundle can be used for transporting speckle images to a detector with a magnifying optics detects speckle images and a computer calculate a temporal speckle intensity autocorrelation function, also known as a g2(t) curve, that provide viscoelastic properties of measured plaque. This process is described, for example, in U.S. Pat. No. 7,231,243, which is herein incorporated by reference in its entirety.

At the distal end of the catheter, the light from the illumination fiber is directly reflected by a mirror surface and illuminated on lumen wall, such as a plaque or a tissue on vessel wall. Multiple scattered lights in a tissue are captured by focusing lens such as a gradient-index (GRIN) lens and imaged on the fiber bundle end face, and transported to the proximal end.

Figure 1A:
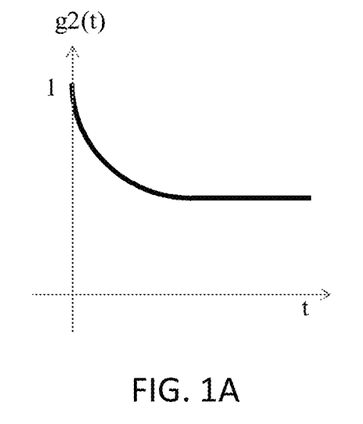
FIG. 1A shows a typical g2(t) curve.

These speckle images are created from a single area in a tissue, and fluctuated along time from $t=t_o$ to $t=t_n$. The speckle image fluctuation can be described by a temporal speckle intensity autocorrelation function named g2(t) curve that compares following images with an initial image at $t=t_o$. FIG. 1A shows a simplified typical g2(t) curve calculated by speckle images.

Figure 1B:
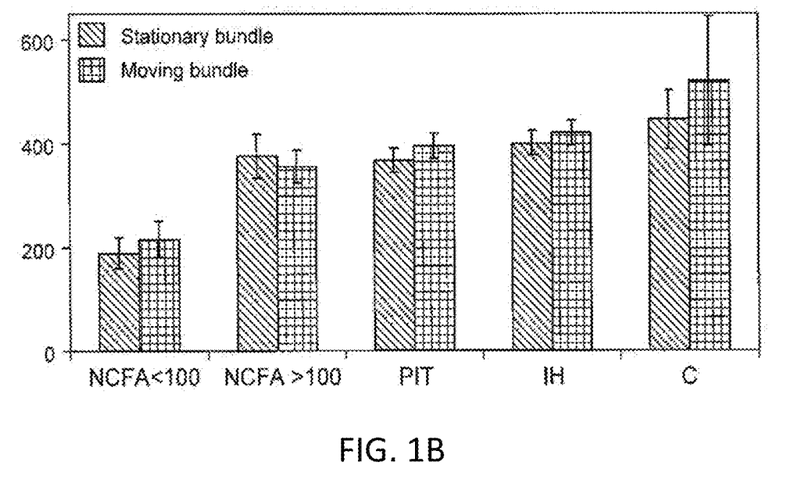
FIG. 1B shows a comparison of T for different types of plaques.

A time constant "T" can be calculated uniquely from a g2(t) curve to evaluate how fast speckle images fluctuated numerically. In coronary artery, there are several types of plaques and some of them are related to AMI. FIG. 1B shows a comparison of τ for plaques where NCFA<100 means necrotic-core fibroatheroma with a minimum fibrous cap thickness <100 um, NCFA>100 means with cap thickness >about 100 um, PIT means pathological intimal thickening, IH means intimal hyperplasia, and C means calcific plaque. NCFA with about 65 μm cap thickness is deemed to be the critical role for plaque rupture. See. U.S. Pat. Pub. 2008/0262359. Thus, an ILSI catheter can be used to distinguish unstable plaques causing AMI in-vivo.

To accomplish an omni-directional viewing catheter for the ILSI catheter with a waveguide which is shown herein as a fiber bundle, several embodiments are described. The first embodiment uses a multi-faceted pyramidal mirror with an illumination switching system (embodiment 1) and second method is using a cone mirror (embodiment 2). The illumination switching system is used to avoid image overlapping from each faces of a pyramidal mirror on a fiber bundle end face.

Figure 2:
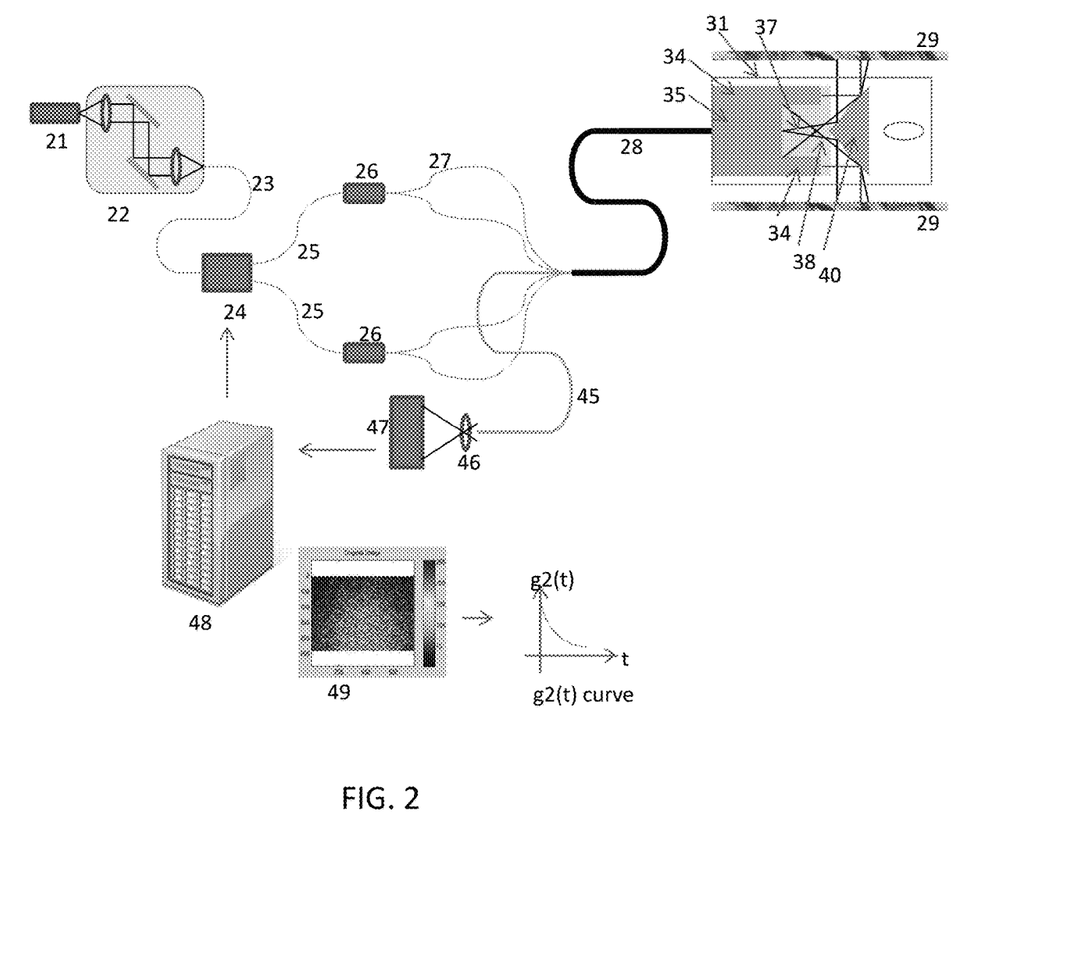
FIG. 2 Schematic diagram of the omni-directional viewing ILSI catheter using 4-faceted pyramidal mirror with an illumination switching system.

FIG. 2 shows a schematic of the omni-directional viewing ILSI catheter of embodiment 1 using 4-faceted pyramidal mirror with an illumination switching system. In this embodiment, the emitted beam from a laser source is coupled with a single mode fiber used as illumination fibers. The single mode fiber is connected with an optical fiber MEMS switching system. This MEMS switching system has one input channel and two output channels, and is controlled by a computer to switch output channels. Two output channels are connected to fiber couplers that split 50:50 intensities. Then, four illumination fibers are incorporated in the ILSI catheter and two of them are switched simultaneously and illuminated on lumen wall, which is a plaque or a tissue on vessel wall in this case.

In further detail for FIG. 2, coherent light, such as laser light, from light source 21 is transmitted via fiber coupling optics 22 through a fiber 23 into an illumination switching system 24 such as a microelectromechanical (MEMS) switching system that and provides two output fibers 25, which pass through fiber couplers 26. The illumination fibers 27 couple into a catheter 28. The distal end of the catheter 28 is shown in an expanded view using the same numbering as in FIG. 3 below, where light from the illumination fiber 34 passes through a circular polarizer 38 and onto a reflector, such as a mirror 40 shown here as a four-faceted pyramidal mirror. From the reflector 40, the light is reflected to a tissue sample 29, such as a layer of static tissue over a layer of moving tissue, such as an atherosclerotic plaque in the lumen wall. An outer sheath 31 (see FIG. 3B for more detail) can be placed directly in contact with sample 29 (near field), or can be positioned a short distance, e.g., 1 mm to 10 cm away from the sample (far field). Light enters sample 29, where it is reflected by molecules, cellular debris, proteins, compounds (e.g., cholesterol crystals), and cellular microstructures (such as organelles, microtubules) within the sample. Light remitted from the sample 29 reflects from mirror 40 through the circular polarizer 38 where it is passed through a focusing optics (GRIN lens) 37 to the fibers bundle 35, and is then transmitted by fiber bundle 2X to a detector that may be, for example, a planar charge-coupled device (CCD), or a linear or two-dimensional detector. The light optionally passes through an aperture or stop that is located between the circular polarizer and GRIN lens. The optional aperture may alternatively be located at the surface (or surfaces) of the reflector 40 or at a common focal plane. Due to interference, a speckle pattern forms at the detector 2X. The resulting speckle pattern is then digitized by an analog-digital converter, exemplified as part of a computer 48, analyzed using the procedures described herein and in U.S. Pat. No. 7,231,243 and in U.S. Patent Pub. No. 2008/0262359 and optionally shown on a display 49 and a $g_2(t)$ curve may then be calculated.

The present invention is particularly useful for in vivo analysis. Thus, the apparatus is particularly adapted for measurement in human or other animal lumen (e.g., blood vessels). In some preferred embodiments, the outer diameter of the apparatus that can be inserted into a lumen is, at most, 2 mm, 1.5 mm, or 1.0 mm, or 990 µm. In some preferred embodiments, the outer diameter of the optics that can be inserted into a lumen (e.g., the fiber bundle, illumination fiber, focusing and reflecting optics) is, at most, 1 mm, 900 µm, 800 µm, 700 µm, 600 µm, 500 µm or less.

Many other types of instruments can be used to gather speckle data. For example, the optics as described herein can be integrated into other types of instruments, such as endoscopes, arthroscopes, or laparoscopes. The optics can also form a stand-alone unit passed into the accessory port of standard endoscopes or laparoscopes, or integrated into another type of catheter, such as dual-purpose intravascular ultrasound catheter. The optics can also include a lens that focuses the remitted light onto the distal ends of the fiber bundle to allow formation of a "near field image" (near the sample sight less than one wavelength) rather than a "far field image" (at the detector set more than a wavelength away from the surface of the tissue).

The circular polarization filter 38 is an optional component that can be used to remove all but a certain type of polarized light. Alternatively, a cross-polarized filter would allow only light having a polarization perpendicular to the incident light to reach the detector, while a parallel polarized filter would allow only light having the same polarization as the incident light to pass. Since multiply scattered light is less likely to retain its initial polarization than single scattered light, polarization filters can be used to bias the data toward multiply scattered or single scattered light. Such bias can be used to deduce information about the structure of the sample, since light which has penetrated deeper into the sample will be more highly scattered than light reflected from the surface or remitted from near the surface.

Instead of a CCD, the detector can be, e.g., a CMOS sensor, a photodiode detector, a photographic plate, an array of photodetectors, or a single detector. The light source can illuminate the sample with continuous light or synchronized pulses.

In this schematic diagram, a 4-faceted pyramidal mirror is chosen, but certainly, any multiple faceted mirrors can be chosen. In the case of even faceted mirrors, two simultaneous illumination switching can be used to reduce measurement time. In the case of odd faceted mirrors, single illumination switching can be used. It is also contemplated to use single illumination switching where even faceted mirrors are used.

Thus, in one embodiment, a 6-faceted pyramidal mirror is used, where the illumination optics and MEMS switching systems are adapted to illuminate, in series, three pairs of opposite facets of the mirror and thus three sections of the lumen wall in series, where, at each point in time, the two opposite faces of the 6-faceted pyramidal mirror are illuminated simultaneously.

In yet another embodiment, an 8-faceted pyramidal mirror is used, where the illumination optics and MEMS switching systems are adapted to illuminate, in series, four pairs of opposite facets of the mirror and thus four sections of the lumen wall in series, where, at each point in time, the two opposite faces of the 8-faceted pyramidal mirror are illuminated simultaneously.

In another embodiment using a 6-faceted pyramidal mirror, the three alternating facets are illuminated simultaneously, where the MEMS switch causes illumination, in series, of the two sets of alternating facets. Similarly for the 8-faceted pyramidal mirror, four facets are illuminated simultaneously, where the four facets are alternating facets and the two sets of alternating facets can be illuminated in series.

In some embodiments, each of the facets of the multi-faceted pyramidal mirror can be illuminated, and then the apparatus is rotated with a non-continuous rotation by approximately $360°/(n*2)$ where n is the number of facets in the mirror.

Figure 8:
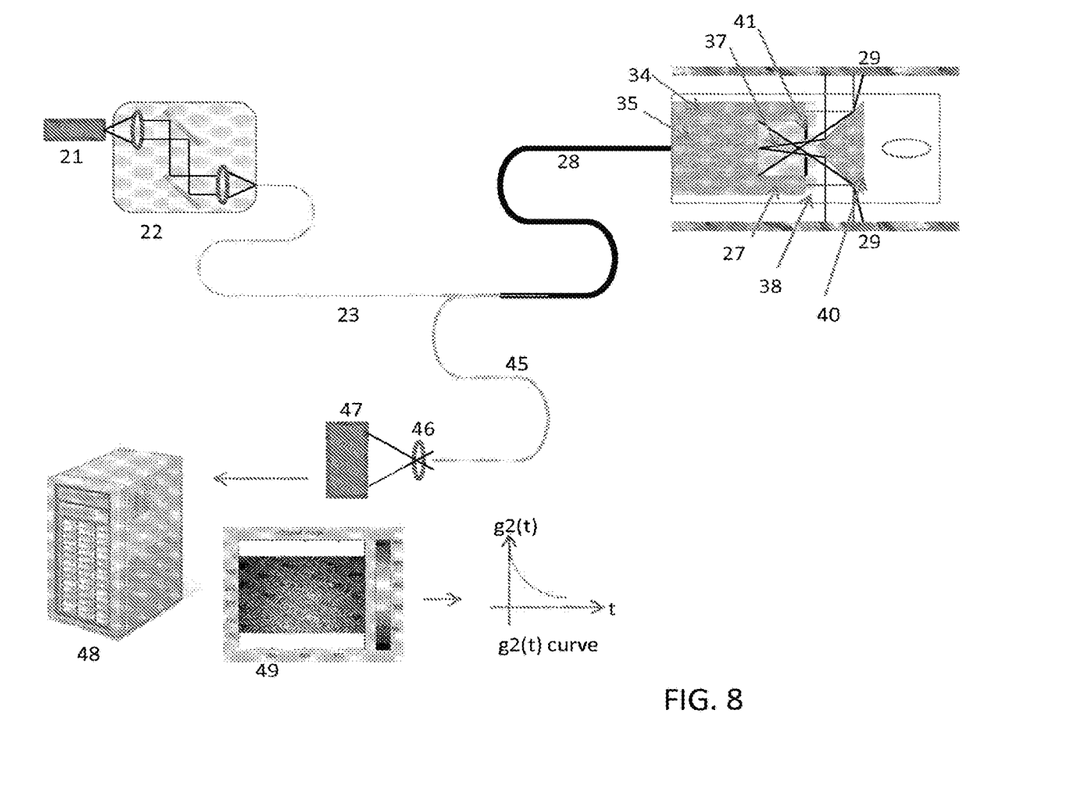
FIG. 8 Schematic diagram of the omni-directional viewing ILSI catheter using cone mirror.

Additional rotations are also contemplated. After measurements at the rotated position, the apparatus may be rotated back to the original position and moved longitudinally along the lumen for additional scans. Preferably, the optical system is designed to optimize such embodiments. For example, an optical stop may be located on the facet as opposed to at the GRIN lens (as shown in FIG. 8 discussed herein below).

In this system, also the fiber bundle is used for transporting speckle images from the distal end to the proximal end. At the proximal end, a detector with a magnifying optics detects speckle images and a computer calculate a temporal speckle intensity autocorrelation function, also known as a $g_2(t)$ curve, that provide us viscoelastic properties of measured plaque.

At the distal end, the lights from the illumination fibers are directly reflected by the 4-faceted pyramidal mirror surface and are illuminated on lumen walls, which are plaques or tissues on vessel walls in this case. Multiple scattered lights in tissues are captured by a GRIN lens and imaged on the fiber bundle end face, and transported to the proximal end.

Figure 3A:
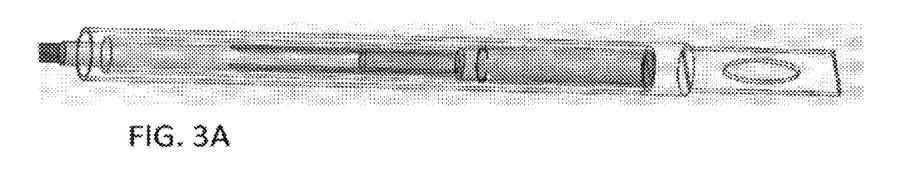
FIGS. 3A-3B. A CAD model for the ILSI catheter distal optics using a 4-faceted pyramidal mirror in perspective view (FIG. 3A) and plan view (FIG. 3B).

To explain the omni-directional viewing ILSI catheter using a multi-faceted pyramidal mirror with an illumination switching system, optical elements organization of the ILSI catheter distal optics are described. FIG. 3A shows a CAD model for the ILSI catheter distal optics using a 4-faceted pyramidal mirror and FIG. 3B shows example dimensions for each optical element.

FIG. 3A shows a CAD model for the ILSI catheter distal optics using a 4-faceted pyramidal mirror. This ILSI catheter incorporates the 4-faceted pyramidal mirror and associated four single mode fibers used for illumination. The rotational angle positions of 4 illumination fibers about longitudinal direction of the ILSI catheter is equivalent to the facets of the 4-faceted pyramidal mirror. The illumination lights passing thorough four different single mode fibers are emitted from the end face of fibers, pass through a circular polarizer, reflected by the 4-faceted mirror, and illuminated on tissues. In the tissues, as described herein, multiple scattering occurs and some parts of scattered lights are scattered backward and are reflected on the 4-faceted mirror again, pass through the circular polarizer, and imaged onto the fiber bundle end face by a GRIN lens. The images on the fiber bundle end face are transferred to a proximal optics through the fiber bundle.

Figure 3B:
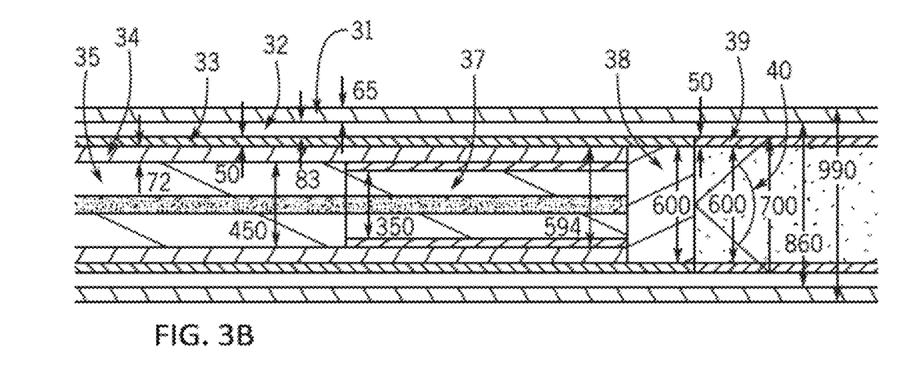

In further detail and in reference to FIG. 3B, an optical catheter 28 exemplified with a multi-faceted pyramid mirror is provided and includes an outer sheath 31 and clearance 32. The drive shaft 33 houses an illumination fiber 34 and a fiber bundle ferrule 35. At the distal end, the fiber bundle ferrule 35 is attached to a focusing optic such as a GRIN lens 37, a circular polarizer 38, and a multifaceted mirror 40 inside an inner sheath 39, which may be transparent. The inner sheath may be particularly adapted to hold a multi-faceted mirror 40, such as a pyramidal mirror. The multi-faceted mirror 40 is shown as a four-faceted pyramid mirror in FIG. 3A. The illumination fiber(s) 34 are can be connected to a fixed optical fiber (not shown) that extends from the catheter proximally to a light source.

Figure 4:
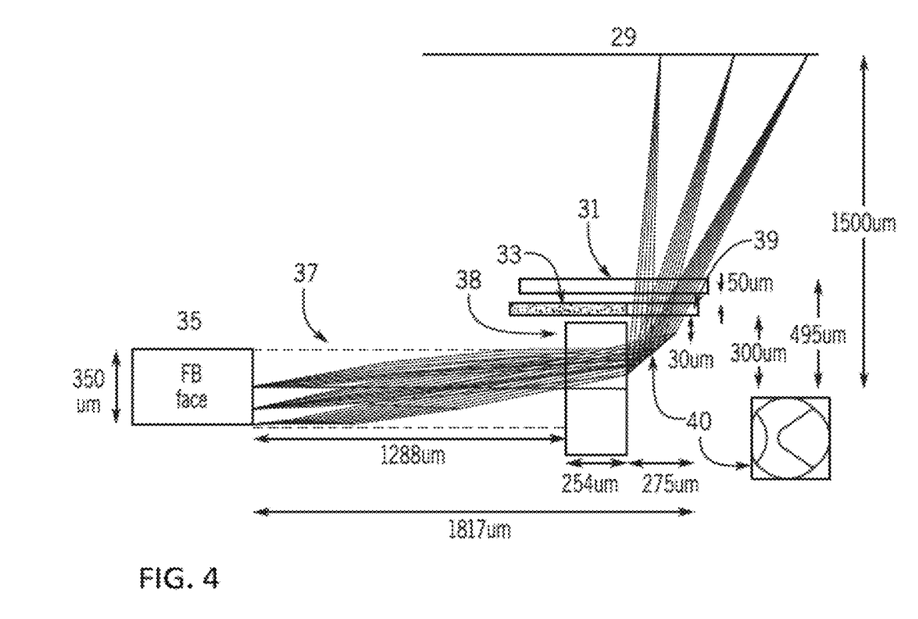
FIG. 4 An optical design for the ILSI catheter distal optics using a 4-faceted pyramidal mirror.

The optical design of the ILSI catheter distal optics with example dimensions is shown in FIG. 4. Thus, there is provided a catheter with optical components having a diameter of less than 1000 μm, less than 800 μm, or less than 600 μm (594 μm as shown) and a catheter including an outer sheath of less than 1500 μm, less than 1250 μm, or less than 1000 μm. Exemplary diameters as shown in FIG. 3B and FIG. 4 are provided to give a total diameter of 990 μm. Other diameters and configurations are also contemplated.

Based on this optical design, the stop of this system can be located at right end face of the GRIN lens and the shape of the pyramidal mirror does not affect any imaging shape. And the field of view (FOV) of this distal optics is limited by the inner sheath transparent area. In this design, to avoid stray light caused by a circular polarizer (CP), The CP's side surface or the inner sheath's partial area is opaque, and FOV is limited to forward vessel wall portion from the CP. The limitation of FOV also improves measurement time as described in the following.

In FIG. 3B, a system stop can be located at the right side of the GRIN lens. Thus, the image obtained through one facet of the pyramidal mirror and the distal optics theoretically has a circular shape since the GRIN lens is cylindrical in shape. But the drive shaft also acts as the aperture stop in addition to the system stop, and the drive shaft vignettes the half of the optical ray bundle. Then the actual image shape on the fiber bundle is half-circle as shown in FIG. 5B.

If the system stop is located at one facet of the pyramidal mirror, the image shape on the fiber bundle end surface is generally the same shape as the facet, and there are no overlapping images. However, in this case, FOV is narrow and total length may need to be longer.

In one exemplary embodiment, which is exemplified by FIG. 4, the focusing optics 37 is a GRIN lens from GRIN-TECH or NSG having a diameter of 350 μm (CA=315 μm). The light is sent through a circular polarizer 38 from American Polarizers, Inc. having 4.2% transmission for double pass (457 mm×609 mm). The inner sheath (FEP AWG23 from Zeus has an inner diameter of 660.4 μm (AWG23) and is 50 μm thick. The outer sheath 39 has an inner diameter of 860 μm, an outer diameter of 990 μm, and a thickness of 65 μm. The reflector 40 used in one particular non-limiting example is a 4-faceted pyramid with 48 degrees, which was formed from a polished brass wire (McMaster). The reflector, in other non-limiting examples, is a 4-faceted pyramid mirror that was formed from a polished glass rod coated with aluminum.

Figure 5A:
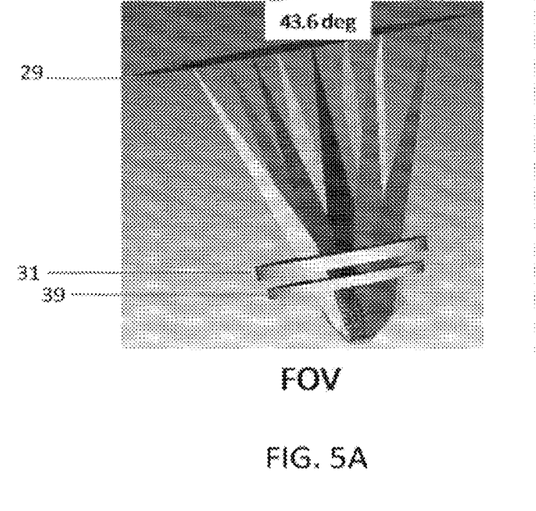
FIG. 5A Field of view at fiber bundle end face.
Figure 5B:
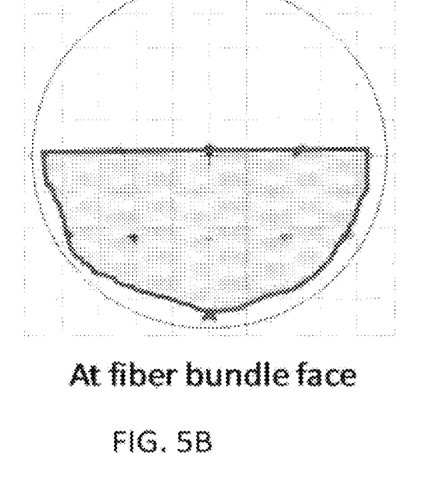
FIG. 5B is the corresponding image shape at fiber bundle end face.

FIG. 5A shows a FOV covered by one facet of the 4-faceted pyramidal mirror and FIG. 5B shows an image shape at fiber bundle end face corresponded to the FOV.

The limitation of FOV cuts a half upper image at fiber bundle end face shown in FIG. 5B, which means that upper side of the fiber bundle end face can be used for an image built by an opposite facet of the pyramidal mirror. On the other hand, since images from neighboring facets overlap to the original image, it should be avoided. To avoid this overlapping images from neighboring facets, illumination lights are switched by an external controller at a proximal optics. Thus, light can be incident on two non-adjacent facets of the mirror at one time and the resulting images will provide a FOV covering most of the fiber bundle. Switching will then allow for each of the facets to be imaged.

As shown in FIG. 5A, the circumferential FOV correspond to one facet is 43.6 deg in this case. This provides a whole circumferential FOV of 174.4 deg (43.6*4 faces), which is equivalent to 48.4% of the full 360 deg. available. This FOV can be improved when number of facet increases, but essentially, the FOV cannot reach to 100% as long as using feasible multiple faceted pyramidal mirror. To achieve 100% circumferential FOV, a non-continuous rotation within partial angle, such as a galvo motor motion, can be incorporated with the ILSI catheter. For example, a galvo motor is located at the proximal end of the catheter and a drive shaft transfer the motion of the galvo motor to the distal end. Since the motion of the fiber bundle is less than cardiac motions in human or animal body and the fiber bundle's proximal end in front of a detector is fixed, speckle images are stable and clear. In some embodiments, the non-continuous rotation is less than 3600, or less than 2700, or less than 180° or less than 90°, or about 45°.

For example, for a four-faceted pyramid, the rotation may be about 45°. This rotation is particularly advantageous since, after imaging through the four facets at one rotational location, rotating the probe about 45° and taking additional images will provide for coverage centered at the locations that were 'dark' in the first set of images. A second rotation, for example, after rotating 45°, a rotation of about 22.5° may be moved. In another embodiment where a six-faceted mirror is used, a rotation of about 30° may be preferred.

Figure 6:
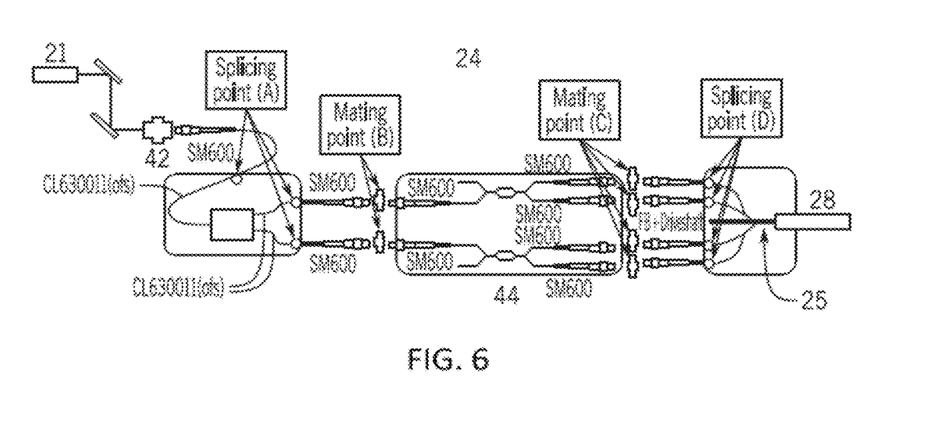
FIG. 6 Illumination switching system at proximal end.

FIG. 6 shows one example of an illumination switching system 24, a MEMS switching system for the ILSI catheter. A light from light source 21, which may be a laser diode 42, is coupled using a fiber coupling lens 42 with a single mode fiber that is a part of a MEMS switching system 24. The fibers are set through a MEMS switch 43, an SM coupler 44. The switching system 24 can change output channels of illumination lights. In this case, two channels are connected with single mode couplers that can split input light to two 50:50 outputs. Then, one light from a laser diode is divided to switchable four illuminations. These four fibers 25 are sent through the catheter 28 where two illuminations are illuminated on tissues simultaneously.

Illuminating only two diagonal pair areas can avoid image overlapping and improve measurement time. As shown in FIG. 5, an image shape correspond to one mirror facet covers half area of the fiber bundle end face, and then two diagonal pair illumination covers full area of the fiber bundle end face. Also, measuring two areas simultaneously makes measurement speed double.

In other similar embodiments (not shown), the illumination switching system can include a MEMS switching system that splits input light into three 33:33:33 outputs. Then, one light from laser diode is divided into switchable six illuminations and three illuminations are illuminated on tissues simultaneously. In other embodiments, the three-way switching system is divided into switchable six illuminations where two three illuminations are illuminated on tissues simultaneously. In other similar embodiments (not shown), one light from laser diode is divided into switchable eight illuminations and either two or four illuminations are illuminated on tissues simultaneously.

Figure 7A:
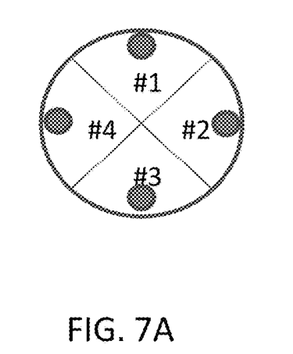
FIGS. 7A-7D Schematic view of four-faceted (FIG. 7A) and six-faceted (FIG. 7C) reflective elements and charts showing the intensity v. time for various embodiments (FIGS. 7B and 7D).
Figure 7B:
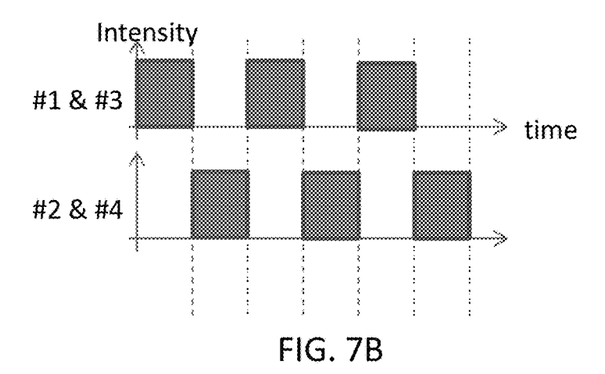
Figure 7C:
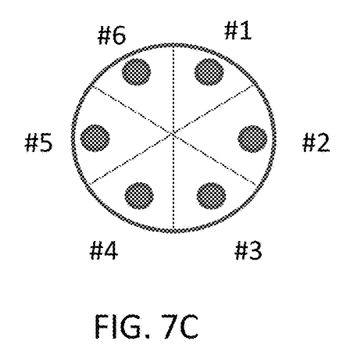
Figure 7D:
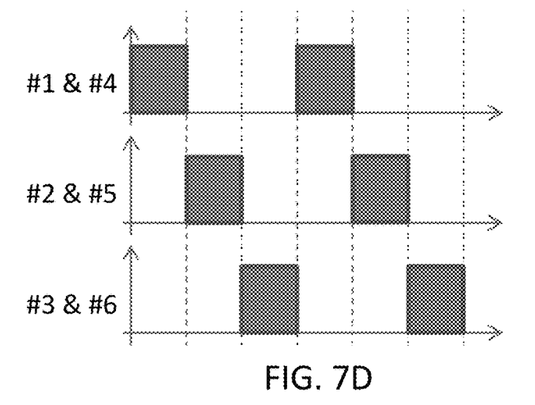

Thus, each illumination fiber, 34 corresponds to each facet of the pyramidal mirror, 40. This configuration, as shown in FIG. 2, can be provided to avoid image overlapping and increase measurement speed, illuminated area is controlled by the switching system. As depicted in FIG. 7, for a four-faceted pyramid (FIG. 7A), when illumination #1 and #3 are on, other #2 and #4 are off (FIG. 7B). When illumination #2 and #4 are on, other #1 and #3 are off. It repeats this cycle. In the case of using 6 illuminations and a two-way switch (FIG. 7C), when illumination #1 and #4 are on, others are off (FIG. 7D). Next, illumination #1 and #4 get off and illumination #2 and #5 get on. Next, illumination #2 and #5 get off and illumination #3 and #6 get on. It repeats this cycle.

FIG. 8 shows a schematic of the omni-directional viewing ILSI catheter using a cone mirror. The main difference between FIG. 8 and prior schematics is using a cone mirror and an aperture at the distal end. A cone mirror can cover entire circumferential FOV of a lumen wall, but an image using a cone mirror has tremendously large astigmatism due to a mirror shape. The astigmatism of the image reflected on around tip area of the cone is relatively large, and it is relaxed around the skirt of the cone mirror.

In operation, as exemplified for ILSI using a cone mirror in FIG. 8, coherent light, such as laser light, from light source 21 is transmitted via fiber coupling optics 22 through an illumination fiber 23 into a catheter 28. The distal end of the catheter 28 is shown in an expanded view using the same numbering as in FIG. 3 above, where light from the illumination fiber 34 passes through a circular polarizer 38 and onto a mirror, 40 shown here as a cone mirror. From the mirror 40, the light is reflected to a tissue sample 29, such as a layer of static tissue over a layer of moving tissue, such as an atherosclerotic plaque in the lumen wall. An outer sheath 31 can be placed directly in contact with sample 29 (near field), or can be positioned a short distance, e.g., 1 mm to 10 cm away from the sample (far field). Light enters sample 29, where it is reflected by molecules, cellular debris, proteins, compounds (e.g., cholesterol crystals), and cellular microstructures (such as organelles, microtubules) within the sample. Light remitted from the sample 29 reflects from mirror 40 through the circular polarizer 38 and through an aperture (or stop) 41 where it is passed through a focusing optics (GRIN lens) 37 to the fibers bundle 35, and is then transmitted by fiber bundle 45 to a detector 47 which may be, for example, a planar charge-coupled device (CCD), or a linear or two-dimensional detector.

Due to interference, a speckle pattern forms at the detector 47. The resulting speckle pattern is then digitized by an analog-digital converter, exemplified as part of a computer 48, analyzed using the procedures described herein and in U.S. Pat. No. 7,231,243 and in U.S. Patent Pub. No. 2008/0262359 and optionally shown on a display 49 and a g2(t) curve is calculated.

Figure 9:
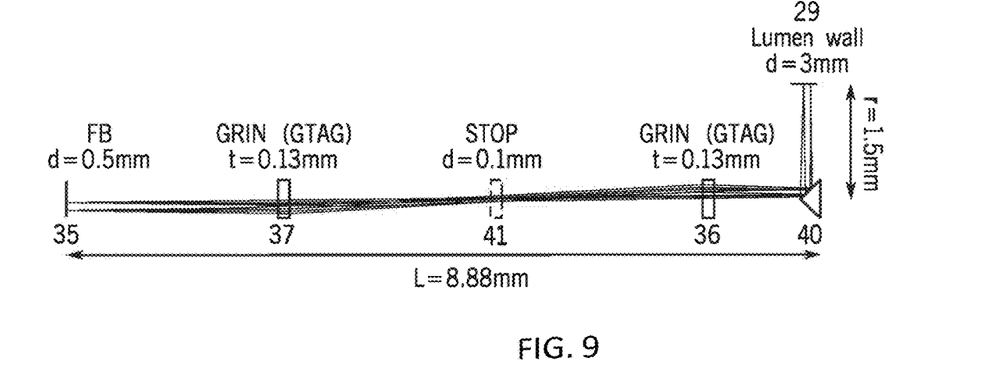
FIG. 9 An optical design for the ILSI catheter distal optics using a cone mirror.

An aperture is used to vignette and improve this astigmatism. FIG. 9 shows an example optical design of the ILSI catheter distal optics using a cone mirror 40.

This optical design chooses double telecentric system and the stop 41 is located between two GRIN lenses (36 and 37). The advantage of this optical design is less distortion independent to the catheter position in the lumen, and less incident angle to the fiber bundle end face 35. Also, this design does not require any illumination switching. An illumination fiber (23, not shown) can be located at the center of the fiber bundle 35 or surrounding of the fiber bundle.

In some preferred embodiments, the fiber optic bundles have reduced inter-fiber crosstalk. Preferably, these fiber optic bundles are leached fiber bundles (such as those sold by SCHOTT). The coupled mode theory (CMT) developed by Snyder (J. Opt. Soc. Am. 62, 1267-1277 (1972)) was applied to determine preferred parameters of the leached fiber optic bundle for use in this embodiment. Using CMT, the influence of multiple fiber bundle parameters on inter-fiber crosstalk and the modulation of transmitted laser speckles were quantified. Furthermore, fiber bundle parameters were defined to considerably reduce the modulation of transmitted speckle patterns caused by mode coupling between and within multi-mode cores. In this analysis, a model multi-core optical fiber system of 7 hexagonally arranged cores embedded in a uniform cladding material was used. CMT was used to evaluate the modulation of laser speckle patterns during transmission through the optical bundles. Thus, each of core diameter, fluctuation in core diameter, numerical aperture, and core spacing have been evaluated to reduce inter-fiber crosstalk.

For some embodiments, particularly where a wavelength of 690 μm is used, the parameters of fiber bundles should include a core diameter of 3.0 μm±0.3 μm, or 3.0 μm±0.2 μm, or 3.0 μm±0.1 μm, or a core diameter of 3.0 μm within measurable error.

A higher NA will confine mode field in the core better but higher NA also increase the number of guided modes and 0.40 NA is the highest currently available contrast of refractive index between core and cladding material of fiber bundles. For some embodiments, particularly where a wavelength of 690 nm is used, the fiber bundle preferably include a numerical aperture of at least 0.35, at least 0.36, at least 0.37, at least 0.38, at least 0.39, or at least 0.40. In one embodiment, the numerical aperture is between 0.37 and 0.41 or between 0.38 and 0.41. While the highest NA for current commercially available fiber optic bundles is approximately 0.40, higher NA are preferred for reducing crosstalk and the invention also contemplates the use of higher NA should they become available, such as a NA of about 0.42, 0.43, 0.44, or 0.45.

An additional parameter that influences mode coupling is the non-uniformity of fibers such as fluctuations of core size and irregular core shape. This non-uniformity could introduce the mismatch in propagation constant $\beta$ between cores and a small amount of mismatch could extensively reduce mode coupling between fibers. For some embodiments, particularly where a wavelength of 690 nm is used, the diameter of the core should have a fluctuation of ±0.02 μm to ±0.4 μm; +0.02 μm to ±0.3 μm, ±0.03 μm to ±0.3 μm; 0.05 μm to ±0.2 μm, or approximately ±0.1 μm. In some embodiments, the core fluctuation is approximately 0.06 μm (2.0%).

A large core-to-core spacing leads to reduced coupling due to the large separation between mode fields because of the less mode field overlaps when the cores are closer. Larger NA indicating larger refractive index contrast between core and cladding material leads to stronger confinement of mode fields and hence reduces overlapping of modal fields of neighboring fibers. For some embodiments, particularly where a wavelength of 690 nm is used, the fiber bundle should include a core spacing of 8.0 μm±0.7 μm, 8.0 μm±0.5 μm, 8.0 μm±0.4 μm, 8.0 μm±0.3 μm, 8.0 μm±0.2 μm, or 8.0 μm±0.1 μm, or 8.0 μm within measurable error.

Thus, in these embodiments, the fiber optic bundles comprise a plurality of core fibers each having: a core diameter of 3.0 μm±0.3 μm with a fluctuation in core diameter of ±0.05 μm to ±0.3 μm, and a numerical aperture of at least 0.35, and the fiber optic bundle having a core spacing of 8.0 μm±0.5 μm. In some embodiments, the fiber bundle has a core diameter of 3.0 μm±0.1 μm with fluctuations in the core size of ±0.1 μm to ±0.2 μm, a core spacing of 8.0 μm±0.5 μm, and a numerical aperture of between 0.38 and 0.41. In yet other embodiments, the same or similar procedures used to obtain these optimized parameters may be used to obtain similar parameters when other wavelengths are used.

The advantage of this invention which achieves omni-directional viewing catheter using a multiple faceted pyramidal mirror with illumination switching and a cone mirror is that it can improve mechanical complexity. Current state of the art has a large barrier to rotate a fiber bundle and then achieve omni-directional viewing. Even if a mechanical complex optical fiber rotary joint can rotate a fiber bundle, the speckle image quality that affects unstable plaque detection becomes unstable and degraded.

The proposed invention of the omni-directional viewing catheter can accomplish stable and clear speckle imaging.

The invention includes an optical system for detecting speckle patterns in a sample. The system has a fiber optic probe as described herein; a coherent or partially coherent light source connected to the central optical fiber within the fiber array; a detector to receive light remitted from the sample; and a processor to process the remitted light and to analyze speckle patterns remitted from the sample. For example, the processor can include reference speckle pattern time constants or a whole library of reference speckle pattern time constants, or reference speckle pattern correlation curves, e.g., for healthy and diseased tissue. The system can also include an analog-digital converter to convert the analog remitted light into a digital signal.

In general, the invention features a method of analyzing tissue, e.g., in vivo, by illuminating a tissue with coherent light, such as laser light, or partially coherent light; receiving light reflected from the tissue at a detector to form a series of speckle patterns; and analyzing changes in the speckle patterns at time intervals sufficient to measure changes caused by motion of objects within the tissue on a microscopic scale, e.g., less than about 1 mm (e.g., less than about 500 or 100 microns), such as Brownian motion of molecules or macromolecules, or motion of cells or cellular organelles, or other non-random forms of motion such as lymph or intracellular transmembrane flow, while eliminating motion on a macroscopic scale, e.g., greater than about 1 mm.

For example, the speckle patterns can be measured at a near field or at a far field and imaged onto the detector. "Near field" is measurement of the speckle distribution less than one wavelength of light from the surface of a tissue, while "far field" speckle is the interference pattern formed greater than one wavelength of light from the surface. The method can further include compensating for macroscopic or extrinsic motion, such as a heartbeat, patient motion, or peristalsis, to isolate the microscopic, e.g., Brownian, motion.

In this method, the illuminating step can include providing an invasive device coupled to a light source, passing the device into a patient, placing the device in proximity to the tissue, and shining coherent light or partially coherent light from the light source onto the tissue.

The apparatus may be an invasive device such as, for example, a catheter, an endoscope, or a laparoscope. The device can be placed in direct contact with the tissue (to measure a near field speckle pattern) or may be a given distance from the tissue (to measure a far field or near field speckle pattern). The device can include a catheter having a first fiber (or fiber array or bundle) that transmits light from the light source to the tissue, and a fiber array or single fiber that receives light remitted from the tissue. The fiber arrays can be one or two-dimensional. After illumination at a position (with our without non-continuous rotation) the apparatus is moved longitudinally along the tissue and additional measurements are taken. This can provide, for example, an image of a full length of a luminal tissue.

An aspect of the present invention provides an apparatus for tissue analysis comprising: an optical fiber bundle, a lens in optical communication with the distal end of the optical fiber bundle, a cone or cone-polygon mirror in optical communication with the lens, an aperture located between the lens and the cone mirror, and one or more illumination fiber(s) in optical communication with the cone mirror, wherein the aperture reduces astigmatism of light reflecting off the cone mirror and into the optical fiber bundle. In some embodiments, the one or more illumination fiber(s) is located in the center of the fiber bundle. In some embodiments, the one or more illumination fiber(s) is aligned as a ring shape around the fiber bundle. The mirror may be a cone mirror, the apparatus may be a double telecentric system, and/or the lens is a GRIN lense. In some embodiments, the apparatus further comprising a circular polarizer between lens and the cone mirror.

In some embodiments, transparent adhesive such as UV curing epoxy may be used in optical ray passing space between the reflector and either the waveguide(s) or other optical elements (e.g., between a circular polarizer and a pyramidal mirror). This adhesive can improve stiffness of the distal optics and position stability of the pyramidal mirror. In addition, in exemplary embodiments, this adhesive has similar index of reflection of a circular polarizer and a tube holding the pyramidal mirror so that back reflections causing image contrast degradation and laser instability can be reduced.

An aspect of the present invention provides a method of tissue analysis comprising: illuminating a cylindrical section of a lumen wall with coherent or partially coherent light by passing the light through a mirror; receiving light reflected from the cylindrical section of a lumen wall at the mirror; receiving light reflected from the mirror at a detector and forming series of speckle patterns; analyzing changes in the speckle patterns at time intervals sufficient to measure changes caused by microscopic motion of objects within the tissue. In some embodiments, the mirror is a multiple faceted pyramidal mirror and in other embodiments, the mirror is a conical mirror and the light reflected from the mirror passes through an aperture. In some embodiments, the light reflected from the mirror passes through a double telecentric lens system.

The analyzing step can include comparing each of the series of speckle patterns to a series of reference speckle patterns, and quantifying the temporal correlation differences between the patterns and the reference patterns. For example, the analyzing step can include digitizing each of the speckle patterns as a function of time and space, and the quantifying step can include evaluating a cross-correlation between the patterns and the reference patterns. The analyzing step can further include determining a decorrelation rate for the speckle patterns, or analyzing spatial characteristics of the speckle pattern to deduce structural and/or biomechanical characteristics of the tissue. Biomechanical characteristics can include, for example, compliance, elasticity, stress, strain, and viscosity. In these methods, speckle pattern data is a snapshot taken at a specific point in time. Speckle pattern correlation data is a measurement of cross-correlation of the speckle pattern as a function of time.

In variations, the method can include illuminating multiple locations of the tissue in succession, forming a separate series of speckle patterns for each respective location of the tissue, and then analyzing each separate series of speckle patterns and comparing the separate series to deduce structural and/or biomechanical differences between the respective locations of the tissue.

In certain embodiments, the method includes gathering reflected light at a light receptor and transmitting the gathered light to the detector, and compensating for macroscopic motion by coupling the receptor to the tissue. Compensating for macroscopic motion can also be done by excluding changes in the speckle patterns caused by non-random motion during the analysis step. Macroscopic or extrinsic motion can also result, for example, from blood flowing between the tissue and the reflector. In those cases, the compensating step can include replacing the blood with a transparent solution and/or eliminating correlated speckle pattern information corresponding to directional blood flow.

In another embodiment, the invention features a method of analyzing a tissue structure, e.g., for determining the susceptibility to rupture of an atherosclerotic plaque having a lipid pool and a fibrous cap. The method includes illuminating the tissue structure, e.g., plaque, with coherent or partially coherent light; receiving light reflected from the tissue structure at a detector to form a series of speckle patterns; gathering speckle pattern data at time intervals sufficient to measure microscopic motion, e.g., Brownian motion or other forms of microscopic motion, within the tissue structure or tissue adjacent the tissue structure, such as a lipid pool; and assessing the tissue structure, e.g., assessing a plaque's vulnerability to rupture from the amount of Brownian motion.

The method can further include analyzing spatial characteristics of the speckle pattern data to determine structural and/or biomechanical characteristics of the tissue structure, e.g., plaque, for example, by assessing the thickness of the tissue structure, e.g., fibrous cap. The thickness of the tissue can be determined by measuring the spatial and temporal decorrelation of the speckle pattern as a function of distance from the incident beam entry point. Near the beam entry point, the speckle pattern will be more stationary. Far away from the bean entry point, the speckle pattern will decorrelate more rapidly. The location of the transition is an indication of thickness. Other methods for determining thickness are described herein. A plaque is considered vulnerable to rupture if the thickness of the fibrous cap is less than about 60 microns. The method can also be used to assess the viscosity of the lipid pool, wherein the plaque is considered vulnerable to rupture if the viscosity of the lipid pool has a time constant of less than about 200 milliseconds, and considered likely to rupture if the viscosity of the lipid pool has a time constant of less than about 100 milliseconds.

The invention also includes a method of detecting a vulnerable atherosclerotic plaque having a lipid pool and a fibrous cap within a blood vessel by illuminating a segment of the blood vessel in vivo with coherent or partially coherent light; receiving light reflected from the interior vessel wall of the segment at a detector to form a series of speckle patterns; gathering speckle pattern data at time intervals sufficient to measure microscopic, e.g., Brownian, motion within the interior vessel wall; and comparing the speckle pattern correlation data to a known speckle pattern time correlation data. One means for comparing the measured speckle pattern correlation data with a reference speckle pattern correlation data is by the time constant, or the time it takes for the speckle pattern to decorrelate by i/e. For example, the decorrelation time constant for any given segment of vessel may be measured and compared to known time constants for normal vessels, atherosclerotic vessels, lipid pools with thick fibrous caps and lipid pools with thin fibrous caps (vulnerable plaques). If the time constant indicates the presence of a lipid pool ($\tau<100$ ms), with a thin fibrous cap, spatial characteristics of the speckle pattern data can be further analyzed to determine structural characteristics of the plaque as described herein. In addition, the first (mean) and second (standard deviation) of the probability distribution function pattern (histogram) of the speckle pattern is unique for different plaque types.

The reflector, which may be a multiple faceted pyramidal mirror, can be fabricated by any method as known in the art and particularly as modified for fabrication of small optics. Each of aluminum, brass, and stainless steel wire were polished to form multiple faceted pyramidal mirrors. Both 3 µm diamond and 0.3 µm $Al_2O_3$ films were used. A 600 µm silica rod was also polished and coated with either Au or Al. Other diameter rods and rods with other compositions and other reflective coating materials may also be used. Both four- and six-faceted mirrors were fabricated by this method and tested. However, other reflectors can be fabricated by these and similar techniques.

To test the reflectors, uniform light was passed through an Air Force Chart before reflecting from the reflector on to a PixeLink camera. In one test, stainless steel was found to have a reflectivity of about 75% at 690 nm. Au coated glass had a reflectivity of about 97% at 690 nm.

In referring to the description, specific details are set forth in order to provide a thorough understanding of the examples disclosed. In other instances, well-known methods, procedures, components and circuits have not been described in detail as not to unnecessarily lengthen the present disclosure.

"Speckle" is an interference phenomenon that occurs when coherent or partially coherent light is reflected from a rough or multiply scattering sample onto a detection plane. A "speckle pattern" is the intensity pattern that results from interference.

"Coherence" is the property of light that allows interference of two or more optical waves. "Partial coherence" refers to waves that can interfere with each other if the path traveled by each wave is equivalent to or within the temporal coherence length of the light at any given point in the specimen.

As used herein, the phrase "full circumference" means at least 50% of the total circumference, or more preferably at least 60%, or at least 70%, or at least 80% and wherein the non-included circumference is distributed around the lumen (i.e., 50% coverage means at least four distinct regions of the lumen spaced around the circumference of the lumen where any single non-imaged area is, at most, 15% of the circumference, and preferably less than 12% or less than 10%.) Thus, the methods as disclosed herein can sequentially illuminate the full circumference of the lumen tissue wall.

As used herein, the phrase, "substantially non-overlapping" as used in context of speckle images not substantially overlapping on a tissue or as reflected on an optical fiber bundles means that most of the image data reflecting from one mirror facet does not overlap with the image data reflecting from a second (or several other) mirror facet(s). Thus, less than 15% of the total light intensity entering the fiber bundle will be overlapping. Preferably, less than 10%, or less than 5%, or less than 2%, or less than 1% of the light intensity will be overlapping. Alternatively, when pull-back is used during imaging, substantially non-overlapping means that the amount of overlap of image data on the fiber bundle is less than the overlapping measuring area on the lumen tissue during the pull-back motion of the catheter. In this case, while substantially non-overlapping image data on the fiber bundle is necessary so as to not to degenerate the speckle image, some overlap is acceptable and even preferred in order to stitch images in post-processing.

As used herein, "tissue" means any biological structure in or on a body. Tissue includes aggregates of cells, growths, and deposits such as plaque that may contain lipids or other components. Specific components of plaques that can be investigated include lipid pools, calcifications, fibrous regions, and fibrous caps.

As used herein, a "double telecentric lens," which may also be referred to a lens having bilateral telecentricity, forms when, for example, a system stop is placed at the common focal plane, resulting in both the entrance and exit pupils being located at infinity. Thus, shifting either the image or object planes does not affect magnification given that double telecentric systems are afocal.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. For example, "about" can mean a range of up to 20% of a given value, and more preferably means a range of up to 10%.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so

What is claimed is:

1. An apparatus for tissue analysis, comprising:
at least a first waveguide and a second waveguide, each configured to provide a luminal tissue with illumination comprising coherent or partially coherent light,
one or more switches configured for switching the illumination of the first and second waveguides,
at least a third waveguide comprising an optical fiber bundle configured to receive light reflected from the luminal tissue,
the optical fiber bundle comprising a plurality of adjacent optical fibers comprising a fiber bundle end face,
a reflector comprising a plurality of facets arranged around a central axis of the apparatus,
the plurality of facets including a first facet and a second facet,
the third waveguide being located on the central axis of the apparatus to receive light reflected from each of the plurality of facets at the fiber bundle end face,
each of the first waveguide and the second waveguide being parallel to the third waveguide and off the central axis of the apparatus,
the first facet configured to reflect light from the first waveguide onto a first section of the luminal tissue and to reflect light from the first section of the luminal tissue onto the third waveguide, and
the second facet configured to reflect light from the second waveguide onto a second section of the luminal tissue and to reflect light from the second section of the luminal tissue onto the third waveguide,
the first section of the luminal tissue being non-overlapping with the second section of the luminal tissue;
a computer adapted to generate intraluminal laser speckle images of the luminal tissue from the light reflected onto the third waveguide without any overlapping images; and
a display to display an intraluminal laser speckle image of the luminal tissue.

2. The apparatus of claim 1, wherein the first and second waveguides configured to provide illumination to the luminal tissue are configured to provide illumination to, in total, at least 120 degrees.

3. The apparatus of claim 1, wherein the first and second waveguides are single mode fibers.

4. The apparatus of claim 1, wherein the one or more switches are micro-electro-mechanical systems (MEMS) switches.

5. The apparatus of claim 1, further comprising a lens in optical communication with a distal end of the optical fiber bundle.

6. The apparatus of claim 1, wherein the reflector comprises a multiple faceted pyramidal mirror comprising a first mirror facet and a second mirror facet, wherein the first mirror facet is in optical communication with the first waveguide, and wherein the second mirror facet is in optical communication with the second waveguide.

7. An apparatus for tissue analysis comprising:
a multiple faceted pyramidal mirror having a plurality of facets arranged around a central axis of the apparatus, each of the plurality of facets including at least a first mirror facet and a second mirror facet,
a first switchable illumination fiber in optical communication with the first mirror facet, and
a second switchable illumination fiber in optical communication with the second mirror facet,
an optical fiber bundle in optical communication with the multiple faceted pyramidal mirror,
wherein the optical fiber bundle comprises a plurality of adjacent optical fibers comprising a fiber bundle end face,
wherein the optical fiber bundle is located on the central axis of the apparatus to receive light from each of the plurality of facets at the fiber bundle end face,
wherein the first and second switchable illumination fibers are parallel to the optical fiber bundle and off the central axis of the apparatus,
wherein the first and second switchable illumination fibers are each adapted to illuminate non-overlapping tissue sections including a first section and a second section,
wherein the first mirror facet reflects light from the first switchable illumination fiber onto the first section and reflects light from the first section onto a distal end of the optical fiber bundle, and
wherein the second mirror facet reflects light from the second switchable illumination fiber onto the second section and reflects light from the second section onto the distal end of the optical fiber bundle,
a detector in optical communication with the proximal end of the fiber bundle,
a computer adapted to calculate a temporal speckle intensity autocorrelation function using light received from the detector to generate an image based on the non-overlapping tissue sections using the temporal speckle intensity autocorrelation function, and
a display to display a laser speckle image based on the non-overlapping tissue sections.

8. The apparatus of claim 7, further comprising a lens located at the distal end of the optical fiber bundle.

9. The apparatus of claim 8, wherein the lens is a gradient-index (GRIN) lens.

10. The apparatus of claim 8, further comprising a circular polarizer between the lens and the pyramidal mirror.

11. The apparatus of claim 7, wherein the multiple faceted pyramidal mirror has four facets.

12. The apparatus of claim 7, wherein the multiple faceted pyramidal mirror has six facets.

13. The apparatus of claim 7, wherein the multiple faceted pyramidal mirror has eight facets.

14. The apparatus of claim 7, wherein the first and second switchable illumination fibers are single mode fibers.

15. The apparatus of claim 7, further comprising a switching system that controls the switching of the first and second switchable illumination fibers.

16. The apparatus of claim 15, wherein the switching system is adapted to illuminate one mirror facet at a time.

17. The apparatus of claim 8, wherein the optical fiber bundle, the lens, and the multiple faceted pyramidal mirror are attached to a drive shaft that is movable within an outer sheath.

18. The apparatus of claim 17, wherein the drive shaft drives a noncontinuous rotation of up to 90°.

19. A method of tissue analysis comprising:
   illuminating, using a probe, at least one first cylindrical section of a lumen wall with coherent or partially coherent light by passing the light from a first switchable illumination source to a first facet of a multiple-faceted pyramidal mirror,
      the multiple-faceted pyramidal mirror being centered around a central axial location of the probe,
         the central axial location of the probe comprising an optical fiber bundle comprising a plurality of adjacent fibers comprising a fiber bundle end face,
   receiving light reflected from the first cylindrical section of the lumen wall at the first facet of the multiple-faceted pyramidal mirror,
      the first facet of the multi-faceted mirror directing the light reflected from the first cylindrical section of the lumen wall to the central axial location of the probe relative to the multi-faceted pyramidal mirror,
         the light reflected from the first cylindrical section of the lumen wall by the first facet being received at the fiber bundle end face in the central axial location;
   illuminating at least a second cylindrical section of a lumen wall with coherent or partially coherent light at a time different from the first illuminating step by passing the light from a second switchable illumination source to at least a second facet of the multiple-faceted pyramidal mirror;
   receiving light reflected from the second cylindrical section of the lumen wall at the second facet of the multiple-faceted pyramidal mirror,
      the second facet of the multi-faceted mirror directing the light reflected from the second cylindrical section of the lumen wall to the central axial location of the probe relative to the multi-faceted pyramidal mirror,
         the light reflected from the second cylindrical section of the lumen wall by the second facet being received at the fiber bundle end face in the central axial location;
   receiving, using the optical fiber bundle, light reflected from the first and second facets of the multiple-faceted pyramidal mirror at a detector and forming a series of speckle patterns that avoid image overlapping from each facet of the multiple-faceted pyramidal mirror; and
   analyzing changes in the speckle patterns at time intervals sufficient to measure changes caused by microscopic motion of objects within the lumen wall.

20. The method of claim 19, wherein the illumination occurs by first illuminating a cylindrical section of a lumen wall through either a single facet of the pyramidal mirror at a time, or multiple facets of the pyramidal mirror at one time, wherein the multiple facets are not adjacent to each other.

21. The apparatus of claim 1, wherein the one or more switches are configured such that the light is reflected from the first section of the luminal tissue onto the third waveguide during a first time period and such that the light is reflected from the second section of the luminal tissue onto the third waveguide during a second time period different from the first time period.

22. The apparatus of claim 21, wherein the plurality of facets further comprises a third facet and a fourth facet,
   wherein the third facet is illuminated by a fourth waveguide and the fourth facet is illuminated by a fifth waveguide, and
   wherein the one or more switches are further configured for switching the illumination of the fourth waveguide and the fifth waveguide,
   wherein the light reflecting from the third facet illuminates a third section of the luminal tissue different from the first section and the second section,
   wherein the light reflecting from the fourth facet illuminates a fourth section of the luminal tissue different from the first section, the second section, and the third section,
   wherein the one or more switches are further configured such that the light is reflected from the third section of the luminal tissue onto the third waveguide during the first time period and the light is reflected from the fourth section of the luminal tissue onto the third waveguide during the second time period, and
   wherein the one or more switches are further configured such that, when at least two of the plurality of facets are illuminated, the at least two facets that are illuminated are separated by at least one facet of the plurality of facets that is not illuminated.

* * * * *

UNITED STATES PATENT AND TRADEMARK OFFICE
CERTIFICATE OF CORRECTION

| | |
|---|---|
| PATENT NO. | : 11,363,945 B2 |
| APPLICATION NO. | : 14/309627 |
| DATED | : June 21, 2022 |
| INVENTOR(S) | : Masaki Hosoda et al. |

It is certified that error appears in the above-identified patent and that said Letters Patent is hereby corrected as shown below:

In the Specification

Column 8, Line 64, "3600" should be --360°--.

Column 8, Line 64, "2700" should be --270°--.

Signed and Sealed this
Sixteenth Day of August, 2022

Katherine Kelly Vidal
*Director of the United States Patent and Trademark Office*